United States Patent
Tsai et al.

(10) Patent No.: US 7,655,258 B2
(45) Date of Patent: Feb. 2, 2010

(54) BIODEGRADABLE COPOLYMER, AND POLYMERIC MICELLE COMPOSITION CONTAINING THE SAME

(75) Inventors: Bin-Hong Tsai, Kaohsiung (TW); Jui-Hsiang Chen, Hsinchu (TW); Muh-Lan Chen, Taipei (TW); Yu-Hua Chen, Taichung (TW); Mei-Jung Liu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 284 days.

(21) Appl. No.: 10/745,975

(22) Filed: Dec. 29, 2003

(65) Prior Publication Data

US 2005/0019303 A1    Jan. 27, 2005

(30) Foreign Application Priority Data

Jul. 21, 2003    (CN) ............................ 92 1 19778

(51) Int. Cl.
*A61K 9/14* (2006.01)
(52) U.S. Cl. .................................... 424/486
(58) Field of Classification Search ............... 424/486; 977/754
See application file for complete search history.

(56) References Cited

U.S. PATENT DOCUMENTS

| | | | |
|---|---|---|---|
| 5,548,035 A | 8/1996 | Kim et al. | |
| 5,578,662 A * | 11/1996 | Bennett et al. | 524/54 |
| 6,322,805 B1 | 11/2001 | Kim et al. | |
| 6,569,528 B2 | 5/2003 | Nam et al. | |
| 6,592,899 B2 | 7/2003 | Fowers et al. | |
| 6,730,334 B2 * | 5/2004 | Zhao | 424/78.3 |
| 2002/0161134 A1 | 10/2002 | Kim et al. | |
| 2003/0181613 A1 * | 9/2003 | Lele et al. | 526/222 |
| 2004/0009229 A1 * | 1/2004 | Unger et al. | 424/486 |

OTHER PUBLICATIONS

Jeon et al., New biodegradable polymers for injectable drug delivery systems, 1999, Jounal of Controled Release, 62, 109-114.*
Kim et al., In vivo evaluation of polymeric micellar paclitaxel formulation toxicity and efficacy, 2001, Journal of Controled Release, 72, 191-202.*
Kwon et al., Block copolymer micelles for drug delivery: loading and release of doxorubicin, 1997, Journal of Controled Release, 48, 195-201.*
Gillies et al. J. Am. Chem. Soc. 2002, 124, 14137-14146.*
XP-002273476, KR2003055927, Dec. 27, 2001.
XP-002273477, KR19980044433, Oct. 23, 1998.
Jiang et al., "Branched Polymeric Micelles: Synthesis and Encapsulation," Chapter 8, American Chemical Society, 1998, pp. 117-124.
Jeong et al., "New biodegradable polymers for injectable drug delivery systems," Journal of Controlled Release, vol. 62, 1999, pp. 109-114.

* cited by examiner

*Primary Examiner*—Michael G. Hartley
(74) *Attorney, Agent, or Firm*—Birch, Stewart, Kolasch & Birch, LLP (57) ABSTRACT

A biodegradable copolymer with a core block comprising bioresorbable hydrophobic polyester segment and from 3 to 10 shell blocks comprising hydrophilic polyethylene glycol segment. The hydrophobic polyester segment and each of the hydrophilic polyethylene glycol segments are linked by a urethane linkage. A polymeric micelle composition containing the copolymer is also provided. The copolymer forms micelles when the concentration of the copolymer in a dispersing medium reaches or exceeds the critical micelle concentration. The micelles possess good drug and bioactive agent delivery characteristics and are suitable for use in drug delivery or cosmetic applications.

21 Claims, 3 Drawing Sheets

BIODEGRADABLE COPOLYMER, AND POLYMERIC MICELLE COMPOSITION CONTAINING THE SAME

This Nonprovisional application claims priority under 35 U.S.C. § 119(a) on Patent Application No(s). 092119778 filed in Republic of China on Jul. 21, 2003, the entire contents of which are hereby incorporated by reference.

BACKGROUND OF THE INVENTION

1. Field of the Invention

The present invention relates to a biodegradable copolymer and a biodegradable polymeric micelle composition containing the copolymer. The biodegradable polymeric micelle composition has good drug and bioactive agent delivery characteristics and is suitable for use in drug delivery or cosmetic applications.

2. Description of the Related Art

Many biodelivery technologies (such as encapsulation and delivery) have been developed for clinical applications, is which prevent pharmaceutical drugs, bioactive substances, or living cells from deterioration by the physiological environment of the body during the course of delivery or to enable slow and stable release in the body. Drugs or bioactive substances are typically encapsulated in bioresorbable polymeric material, such as, poly(lactic acid) (PLA), poly(glycolic acid) (PGA), or lactic acid/glycolic acid copolymer (PLGA) in many commercialized techniques before being administrated to organisms.

PLA and PGA, linear polymeric material, have been used mainly for drug and bioactive substance encapsulation and delivery. However, the encapsulation efficiency of hydrophilic drugs and peptides with high molecular weight are poor due to hydrophobicity. Therefore, many researches are oriented to amphiphilic biodegradable material to overcome this problem.

A. S. Sawhney et al., Macromolecules, Vol 26, No. 4, 581-589 (1993) disclose macromers having a polyethylene glycol central block, extended with oligomers of α-hydroxy acids such as oligo(D,L-lactic acid) or oligo(glycolic acid) and terminated with acrylate groups. Using photoinitiators, these multifunctional macromers can be crosslinked under ultraviolet. The rates of biodegradation upon hydrolysis can be tailored by appropriate choice of the PEG and the oligo(α-hydroxy acid) from less than 1 day to up to 4 months.

Okada et al., in Japanese Patent 2-78629 (1990), disclose a segment-type linear block copolymer formed from PLA or PLGA and PEG. The molecular weight range for PLGA is 400 to 5,000 and for PEG, 200 to 2,000. The reaction is performed under high temperature and the reaction product could precipitate and form a hydrogel in water above room temperature.

T. Matsuda, *ASAIO Journal*, M512-M517 (1993) used a biodegradable polymeric gel to deliver a potent peptidyl antiproliferative agent. The gel was a highly viscous fluid of a linear block copolymer composed of PLA and PEG block segments and used as a drug carrier.

L. Martini et al., *J. Chem. Soc., Faraday Trans.*, 90(13), 1961-1966 (1994) synthesized very low molecular weight ABA type tri-block copolymers by copolymerizing hydrophobic poly(ε-caprolactone) (PCL) block and hydrophilic PEG block, forming a PCL-PEG-PCL tri-block copolymer. Different cloud points were observed with various components. For example, the cloud points of 2 wt % aqueous solutions of the copolymers were 65° C. and 55° C. for PCL-PEG-PCL (450:4000:450) and PCL-PEG-PCL (680:4000:680), respectively. When the molecular weight of PCL was higher, the in vivo degradation rate was slower. A slow degradation was favorable to the drug release control efficiency.

U.S. Pat. No. 6,201,072 issued to MacroMed Company discloses an ABA- or BAB-linear type tri-block copolymer containing a biodegradable polyester (block A) and PEG (block B). The tri-block copolymer is water soluble and possesses reverse thermal gelation properties when the copolymer molecular weight is between 2000 and 4990 and wt % of the hydrophobic segment is between 51 to 83%. A drug delivery composition containing said copolymer is also disclosed. ReGel®, an injectable drug release system developed using PLA-PEG-PLA tri-block copolymer by MacroMed company has been approved by the FDA for years.

In view of the above description, a linear amphiphilic copolymer has been disclosed, but neither a branched amphiphilic copolymer having a hydrophobic segment as a core nor a polymeric micelle composition containing a linear or branched amphiphilic copolymer in use of drug delivery has been disclosed.

G. S. Kwon et al., in *Pharmaceutical Research*, Vol. 12, No. 2, 192-195 (1995) and *Journal of Controlled Release*, Vol. 48, 195-201 (1997) reported micelles of PEO-PBLA copolymer with a diameter of about 20 to 40 nm. The encapsulating rate for the micelles to encapsulate a highly lipid soluble antitumor agent, adriamycin, could be 5-12% (w/w). Compared with un-encapsulated adriamycin, the drug encapsulated with PEO-PBLA copolymer exhibited an extended recycling period in vivo and an improved phagocytic efficiency on cancer cells. In addition, the degradation rate of the drug decreased after encapsulation, thus, the micelles could be deemed as a storage unit for the drug and a long-term release effect could be achieved.

T. Minko et al., *International Journal of Cancer*, Vol. 86, 108-117 (2000) reported an ex vivo experiment using human ovarian carcinoma cell line and the comparison of administrating an antitumor drug, adriamycin (i.e. doxorubicin), by means of conventional methods and by means of micelles of HPMA copolymer with adriamycin attached. The result indicated a higher antitumor activity and lower systemic toxicity of HPMA copolymer-bound adriamycin when compared with free adriamycin.

S. C. Kim et al., *Journal of Controlled Release*, Vol. 72, 191-202 (2001) reported micelles formed by encapsulating paclitaxol in mPEG-PDLLA copolymer molecules. The result of the experiment for the ovarian carcinoma cell line and the human breast cancer cell line indicated that the dosage form of paclitaxol in the micelles reduced cytotoxicity, improved maximum tolerated dose (MTD), improved median lethal dose ($LD_{50}$) and improved antitumor activity, as compared with un-encapsulated paclitaxol.

SUMMARY OF THE INVENTION

Accordingly, an object of the invention is to provide a biodegradable copolymer. When the biodegradable copolymer is in an aqueous medium in a concentration higher than its critical micelle concentration in the aqueous medium, it forms micelles which enable hydrophobic compounds, such as, pharmaceutical drugs and bioactive substances, to have good drug delivery properties and are suitable for use in drug delivery systems or cosmetic applications.

Another object of the invention is to provide a biodegradable polymeric micelle composition. The biodegradable polymeric micelle composition enables the encapsulated hydrophobic compounds, such as, pharmaceutical drugs and bioactive substances, to have good drug delivery properties and is suitable for use in drug delivery systems or cosmetic applications.

The biodegradable copolymer of the present invention has the formula:

wherein C is a core block comprising a bioresorbable hydrophobic polyester segment, S is a shell block comprising a hydrophilic polyethylene glycol segment, n is an integer of 3 to 10, and the hydrophobic polyester segment and the hydrophilic polyethylene glycol segment are linked by a urethane linkage.

The biodegradable polymeric micelle composition of the present invention comprises a copolymer having the formula:

wherein C is a core block comprising a bioresorbable hydrophobic polyester segment, S is a shell block comprising a hydrophilic polyethylene glycol segment, n is an integer of 2 to 10, and the hydrophobic polyester segment and the hydrophilic polyethylene glycol segment are linked by a urethane linkage; and an aqueous medium; wherein, the concentration of the copolymer is more than the critical micelle concentration thereof in the aqueous medium and the copolymer is dispersed in the aqueous medium to form micelles.

The copolymer of the present invention is amphiphilic, i.e. in the copolymer molecule, the hydroxyl end group is hydrophilic and the ester end group is hydrophobic. Therefore, the copolymer can form micelles which can encapsulate a hydrophobic compound such as a drug and bioactive substance. The release rate of the encapsulated compound (such as a drug and bioactive substance) can be regulated by altering the ratio of the amount of the hydrophilic component to the amount of the hydrophobic component, the morphology (linear or branched and the number of branches), the concentration, the molecular weight, and the molecular weight distribution of the copolymer. The present invention can also overcome the problem of poor encapsulation efficiency of the hydrophilic drugs and/or the peptide bioactive substances with relatively high molecular weight encountered by the linear polymer such as PLA and PGA having relatively high hydrophobicity when employed in drug and bioactive substance encapsulation and delivery.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

DETAILED DESCRIPTION OF THE INVENTION

The novel biodegradable copolymer of the present invention has a core block and a plurality of shell blocks and can be presented by the formula:

wherein the number of shell blocks S may be 3 to 10 (that is, n is an integer between 3 and 10, and preferably 3 to 6. Each shell block S is linked to the core block C by a covalent bond. Thus, the microscopic molecule structure of the copolymer is star shaped; therefore herein the copolymer is referred to as a "star copolymer".

"Biodegradable copolymer" is defined herein as a copolymer which can chemically break down or degrade within the body to form nontoxic components.

The core block C comprises a bioresorbable hydrophobic polyester segment. Herein, "bioresorbable" means the property which a material has enables the material to be absorbed in an organism. Suitable bioresorbable hydrophobic polyester can be, but not limited to, a homopolymer or copolymer synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, γ-butyrolactone, γ-hydroxy butyric acid, δ-valerolactone, δ-hydroxy valeric acid, hydroxybutyric acids, or malic acid. Among them, polycaprolactone is most preferred. The average molecular weight of the bioresorbable hydrophobic polyester is preferably 200 to 10000, and more preferably 250 to 5000.

The shell block S comprises a hydrophilic polyethylene glycol (PEG) segment. The average molecular weight of the hydrophilic polyethylene glycol is preferably 200 to 10000, and more preferably 250 to 7000.

The linkage of the shell block S, hydrophobic polyester, and the core block C, hydrophilic polyethylene glycol, is formed through a urethane linkage.

It is noted that a mixture of the biodegradable copolymer of the present invention in water with a solid content of 20% can undergo a phase transformation with a change in temperature. For example, the mixture, exhibiting a white viscous liquid form of micelle per se at room temperature, turns into a transparent liquid in an ice bath and white precipitates occur upon heating due to the separation of the copolymer and water, and these phenomena are reversible and contrary to the common phenomenon of solubility for a normal substance in a solvent that dissolution occurs upon heating and precipitation occurs at low temperature.

The biodegradable copolymer of the present invention presents no cytotoxicity in a physiological environment and exhibits white color in an aqueous medium (such as water) which was characterized to be micelles. The critical micelle concentration is low. The micelles are useful as vehicles in a bio-delivery system to encapsulate hydrophobic compounds, for example, drugs (such as protein complexes, gene drugs, hormone drugs, and anti-cancer drugs) or bioactive substances and to enable them to have a stable effect.

Accordingly, in other aspects, the present invention relates to a biodegradable polymeric micelle composition, which comprises:
(a) a copolymer which is the star-shaped biodegradable copolymer having the formula C—(S)$_n$ (wherein n is an integer of 3 to 10) of the present invention as described above or the biodegradable linear tri-block copolymer S—C—S. C and S are defined as above, and
(b) an aqueous medium, such as water, which enables the biodegradable copolymer to disperse therein.

The copolymer is dispersed in the aqueous medium. When the concentration of copolymer is higher than the critical micelle concentration, the copolymer forms micelles. The critical micelle concentration is generally between 0.001 and 0.5 weight percent. The size of the micelle is generally between 20 nm and 800 nm in diameter.

As mentioned above, the biodegradable copolymer comprised in the biodegradable polymeric micelle composition can be a linear tri-block copolymer (S—C—S) as well as the star-shaped biodegradable copolymer of the present invention. U.S. Pat. No. 6,201,072 discloses an A—B—A- or B—A—B-linear tri-block copolymer containing a biodegradable polyester (block A) and PEG (block B). However, it does not disclose the application of the tri-copolymer in the micelle composition as described in the present invention nor does it mention the micelle structure. In the present invention, the inventors found that the star-shaped biodegradable copolymer, as well as the linear tri-block, can form micelles in a medium. Thus the micelle composition of the present invention can be formed from the linear tri-block copolymer or the star-shaped biodegradable copolymer and a medium.

The micelle composition of the present invention can encapsulate drugs in the micelles. For example, when the aqueous medium is water, the hydrophilic ends of the copolymer molecules outwardly contact with water molecules and the hydrophobic ends aggregate inwardly, thus forming micelles which encapsulate hydrophobic compounds, drugs, or bioactive substance therein.

The biodegradable copolymer of the present invention can be made by the steps as follows.

A suitable amount of DBTDL (dibutyltin dilaurate) and diisocyanate are added to methoxy-polyethylene glycol dissolved in solution. The mixture is heated and the reaction is performed in a nitrogen atmosphere. Then, polyester-diol or -polyol are added and the temperature for reaction is elevated. The product is purified and the structure may be identified using $^1$H NMR (CDCl$_3$, 400 MHz).

The copolymer obtained using polyester-diol is S—C—S type tri-copolymer in a linear structure. The novel type or type star-shaped copolymer of the present invention can be obtained using polyester-polyol, such as polyester-triol and polyester-tetraol.

Polyester-polyol, such as polyester-triol and -tetraol, can be prepared by referring to the method as described in Preparations A and B. The schematic structure of the polyester-triol obtained is shown as follows:

The biodegradable copolymer of the present invention shows no cytotoxy determined according to the method described in the ASTM F895 Standard Test.

The biodegradable polymeric micelle composition can be formed by mixing the copolymer in an aqueous medium in a concentration higher than the critical micelle concentration. The critical micelle concentration can be calculated by means of interpolation in the plotting of the absorbance at UV-VIS wavelength versus the concentration of the copolymer in the medium.

The application of the biodegradable polymeric micelle composition for the encapsulation of hydrophobic compound can be achieved by the process described as follows.

Hydrophobic compounds (such as hydrophobic drugs) and the copolymer are dissolved in a solvent. The resulting mixture was vacuumed at 60° C. by means of rotary evaporation to form a colloid. Pure water was added to the colloid at 60° C., forming micelles encapsulating the drug for the application in drug delivery in the present invention. The resultant may be freeze-dried for storage and added water as a medium to form micelles in liquid type before the administration. The administration can be oral, topical, injected, or by another suitable method.

EXAMPLES

Preparation A The Synthesis of Polycaprolactone Triol (PCL-Triol) (Molecular Weight=2000)

200 g (1.7522 moles) of ε-caprolactone monomer (manufactured by Aldrich Co.) was placed in a reactor, and 23.51 g (0.175 mole) of initiator trimethylolpropane and 0.567 ml (1.75×10$^{-3}$ mole) of stannous 2-ethylhexanoate were added into the reactor. The reaction was performed in a nitrogen atmosphere and the temperature was set at 120° C. After 1.5 hours of reaction, the reaction was rapidly cooled down to room temperature. The precipitates were purified using ether and then vacuumed to remove solvent, yielding a product characterized by $^1$H NMR (CDCl$_3$, 400 MHz) to be polycaprolactone triol.

Preparation B The Synthesis of Polycaprolactone Tetraol (Molecular Weight=2000)

200 g (1.7522 moles) of ε-caprolactone monomer was placed in a reactor, and 28.9 g (0.175 mole) of initiator pentaerythritol (molecular weight=165.15) and 0.567 ml (1.75×10$^{-3}$ mole) of stannous 2-ethylhexanoate were added into the reactor. The reaction was performed in a nitrogen atmosphere and the temperature was set at 120° C. After 1.5 hours of reaction, the reaction was rapidly cooled down to room temperature. The precipitates were purified using ether and then vacuumed to remove solvent, yielding a product, polycaprolactone tetraol.

Examples 1 to 6

The Production of the Biodegradable Copolymer of the Present Invention

Example 1

The Production of Tri-PEG350-PCL900 Star Copolymer 45.6 g (0.27 mole) of hexamethylene diisocyanate and 200 µl of DBTDL were added to 100 g (0.286 mole) of methoxy-polyethylene glycol (molecular weight=350) dissolved in 150 g of toluene. The temperature was set at 60° C. and the reaction was performed in a nitrogen atmosphere. After 2 hours of reaction, 81.51 g (0.091 mole) of PCL-triol (molecular weight=900) and 100 g of toluene were added, and the reaction was continued for 24 hours. Then, the reaction was quenched by dibutylamine (DBA) to completely consume the NCO groups remaining in the reactor. The resultant was precipitated by ether at low temperature, washed repeatedly, and vacuumed until dry, yielding a star copolymer having a formula of $C-(S)_3$ as a powder, herein referred to as "Tri-PEG350-PCL900".

Figure 1:
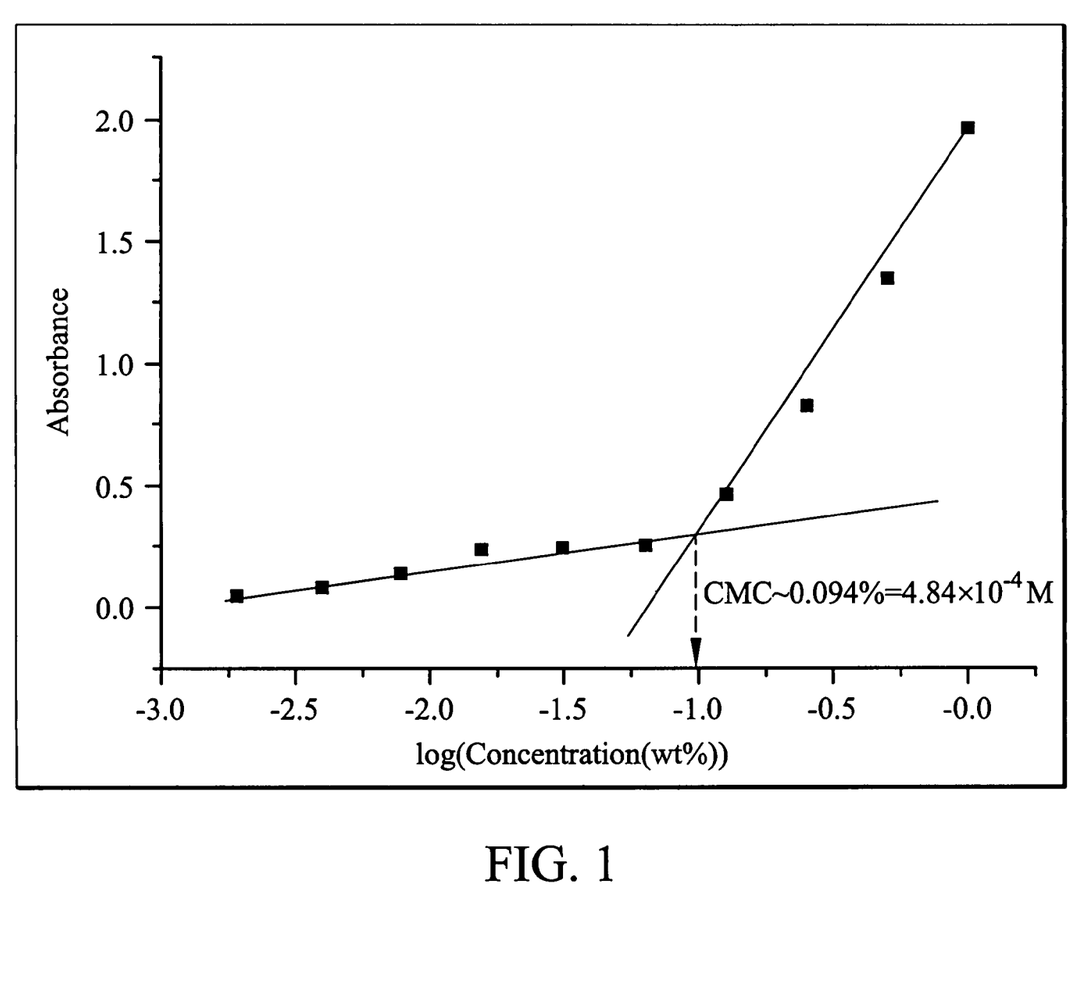
FIG. 1 is a plot obtained by plotting the absorbance at a 356 nm wavelength of a UV-VIS spectrometer versus the logarithm of the concentration of the Tri-PEG350-PCL900 starlike copolymer obtained from Example 1.

The determination of critical micelle concentration (CMC):

The star copolymer obtained from Example 1 was dissolved in a 4 µM diphenyl hexatriene (DPH) (a hydrophobic fluorescent dye) aqueous solution to concentrations of 0.001 wt %, 0.005 wt %, 0.01 wt %, 0.025 wt %, 0.05 wt %, 0.1 wt %, 0.5 wt %, and 1 wt %, respectively. The absorbance at 412 nm of each resulting mixture was determined using a UV-VIS spectrometer. A graph was obtained by plotting absorbance versus concentration, as shown in FIG. 1. The critical micelle concentration was calculated to be about 0.094 wt %, i.e. $4.84 \times 10^{-4}$ M, by means of interpolation.

Example 2

The Production of Tri-PEG5000-PCL900 Star Copolymer 3.19 g (0.019 mole) of hexamethylene diisocyanate and 200 µl of DBTDL were added to 100 g (0.02 mole) of methoxy-polyethylene glycol (molecular weight=5000) dissolved in 100 g of toluene. The temperature was set at 60° C. and the reaction was performed in a nitrogen atmosphere. After 2 hours of reaction, 5.7 g (0.0063 mole) of PCL-triol (molecular weight=900) and 6 g of toluene were added, and the reaction was continued for 24 hours. Then, the reaction was quenched by DBA. The resultant was precipitated by ether at low temperature, washed repeatedly, and vacuumed until dry, yielding a star copolymer having a formula of $C-(S)_3$ as a powder, herein referred to as "Tri-PEG5000-PCL900".

The CMC of the product was about 0.127 wt %, i.e. $7.99 \times 10^{-5}$ M, determined by the method as described in Example 1.

Example 3

The Production of Tri-PEG2000-PCL300 Star Copolymer 8 g (0.0475 mole) of hexamethylene diisocyanate and 200 µl of DBTDL were added to 100 g (0.05 mole) of methoxy-polyethylene glycol (molecular weight=2000) dissolved in 110 g of toluene. The temperature was set at 60° C. and the reaction was performed in a nitrogen atmosphere. After 2 hours of reaction, 4.75 g (0.016 mole) of PCL-triol (molecular weight=300) and 5 g of toluene were added, and the reaction was continued for 24 hours. Then, the reaction was quenched by DBA. The resultant was precipitated by ether at low temperature, washed repeatedly, and vacuumed until dry, yielding a star copolymer having a formula of $C-(S)_3$ as a powder, herein referred to as "Tri-PEG2000-PCL300".

The CMC of the product was about 0.126 wt %, i.e. $2 \times 10^{-4}$ M, determined by the method as described in Example 1.

Example 4

The Production of Tri-PEG5000-PCL300 Star Copolymer 3.2 g (0.019 mole) of hexamethylene diisocyanate and 200 µl of DBTDL were added to 100 g (0.02 mole) of methoxy-polyethylene glycol (molecular weight=5000) dissolved in 105 g of toluene. The temperature was set at 60° C. and the reaction was performed in a nitrogen atmosphere. After 2 hours of reaction, 1.9 g (0.006 mole) of PCL-triol (molecular weight=300) and 2 g of toluene were added, and the reaction was continued for 24 hours. Then, the reaction was quenched by DBA. The resultant was precipitated by ether at low temperature, washed repeatedly, and vacuumed until dry, yielding a star copolymer having a formula of $C-(S)_3$ as a powder, herein referred to as "Tri-PEG5000-PCL300".

The CMC of the product was about 0.14 wt %, i.e. $9.15 \times 10^{-5}$ M, determined by the method as described in Example 1.

Example 5

The Production of Tri-PEG350-PCL300 Star Copolymer 45.6 g (0.27 mole) of hexamethylene diisocyanate and 200 µl of DBTDL were added to 100 g (0.286 mole) of methoxy-polyethylene glycol (molecular weight=350) dissolved in 150 g of toluene. The temperature was set at 60° C. and the reaction was performed in a nitrogen atmosphere. After 2 hours of reaction, 27 g (0.09 mole) of PCL-triol (molecular weight=300) and 30 g of toluene were added, and the reaction was continued for 24 hours. Then, the reaction was quenched by DBA. The resultant was precipitated by ether at low temperature, washed repeatedly, and vacuumed until dry, yielding a star copolymer having a formula of $C-(S)_3$ as a powder, herein referred to as "Tri-PEG350-PCL300".

The CMC of the product was about 0.0125 wt % determined by the method as described in Example 1.

Example 6

The Production of Tri-PEG2000-PCL300 Star Copolymer 8 g (0.0475 mole) of hexamethylene diisocyanate and 200 µl of DBTDL were added to 100 g (0.05 mole) of methoxy-polyethylene glycol (molecular weight=2000) dissolved in 150 g of toluene. The temperature was set at 60° C. and the reaction was performed in a nitrogen atmosphere. After 2 hours of reaction, 14.25 g (0.016 mole) of PCL-triol (molecular weight=300) and 100 g of toluene were added, and the reaction was continued for 24 hours. Then, the reaction was quenched by DBA. The resultant was precipitated by ether at low temperature, washed repeatedly, and vacuumed until dry, yielding a star copolymer having a formula of C–(S)$_3$ as a powder, herein referred to as "Tri-PEG2000-PCL300".

The CMC of the product was about 0.0325 wt % determined by the method as described in Example 1.

Cytotoxicity Assay:

The cytotoxicity response indices of the star copolymers obtained from Examples 1 to 6 were determined by the method described in the ASTM F895 Standard Test using L929 fibroblast. All of the results showed no cytotoxity.

Preparation 1 The Production of PEG2000-PCL530-PEG2000 Tri-Block Copolymer

A suitable amount of DBTDL was added to 100 g (0.05 mole) of methoxy-polyethylene glycol (molecular weight=2000) dissolved in 200 ml of dimethylformamide (DMF), immediately followed by the addition of 7.98 g (0.0475 mole) of hexamethylene diisocyanate (HDI). The temperature was set at 50° C. and the reaction was performed in a nitrogen atmosphere. After 5 hours of reaction, 13.25 g (0.025 mole) of PCL-diol (molecular weight=530) was added, the temperature was raised to 100° C., and the reaction was continued overnight. Then, the reaction was quenched by DBA. After the resultant was cooled down, it was precipitated by 1000 ml of ether, and the resulting precipitates were dissolved in DMF and precipitated from ether. The precipitation process was repeated three times. Then the precipitates were vacuumed until dry, yielding a product characterized by $^1$H NMR (CDCl$_3$, 400 MHz) to be a PEG2000-PCL530-PEG2000 tri-block copolymer.

Figure 2:
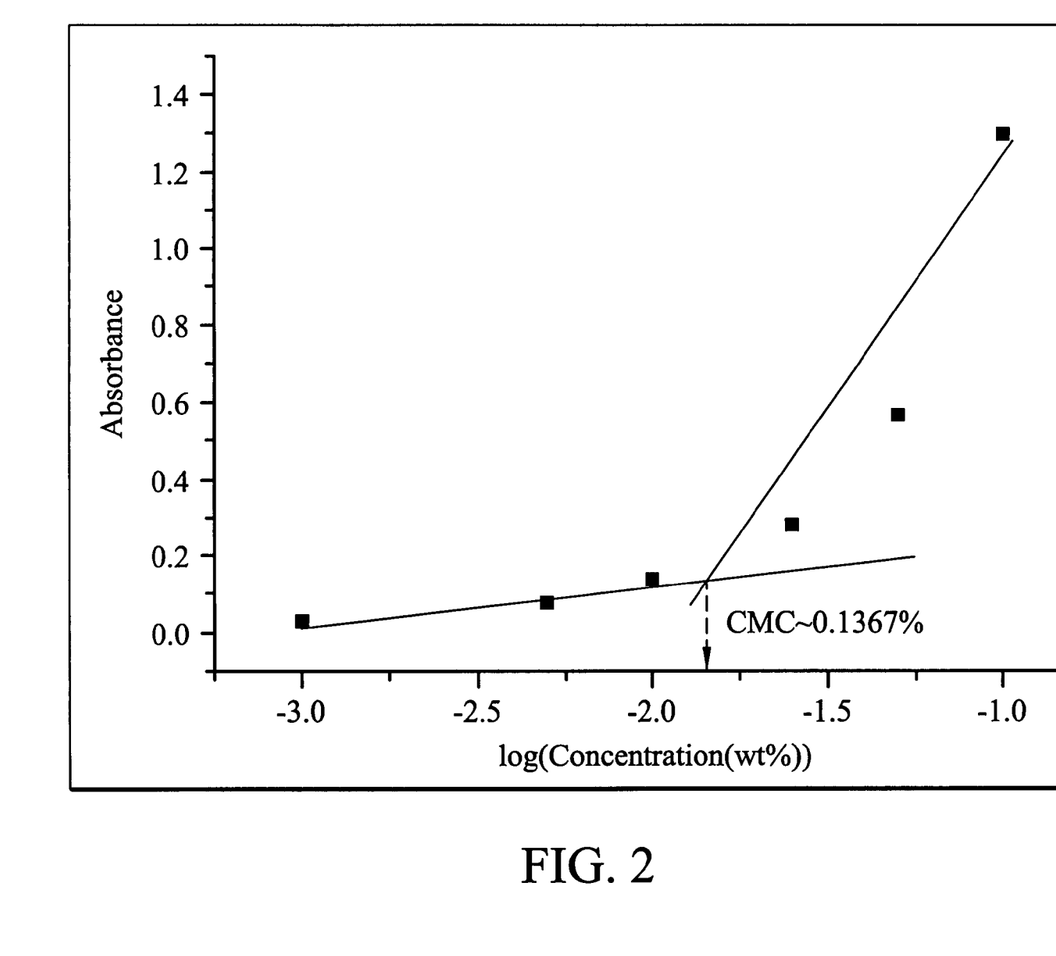
FIG. 2 is a plot obtained by plotting the absorbance at a 356 nm wavelength of a UV-SIV spectrometer versus the logarithm of the concentration of the PEG2000-PCL530-PEG2000 tri-block copolymer obtained from Preparation 1.

The CMC of the product was about 0.1367 wt % determined by the method as described in Example 1, as shown in FIG. 2.

Preparation 2 The Production of PEG2000-PCL1250-PEG2000 Tri-Block Copolymer

Suitable amount of DBTDL was added to 200 g (0.1 mole) of methoxy-polyethylene glycol (molecular weight=2000) dissolved in 400 ml of DMF, immediately followed by the addition of 14.96 g (0.095 mole) of HDI. The temperature was set at 50° C. and the reaction was performed in a nitrogen atmosphere. After 5 hours of reaction, 59.375 g (0.0475 mole) of PCL-diol (molecular weight=1250) was added, the temperature was raised to 100° C., and the reaction was continued overnight. Then, the reaction was quenched by DBA. After the resultant was cooled down, it was precipitated by 2000 ml of ether, and the resulting precipitates were dissolved in DMF and precipitated from ether. The precipitation process was repeated three times. Then the precipitates were vacuumed until dry, yielding a PEG2000-PCL1250-PEG2000 tri-block copolymer.

The CMC of the product was about 0.058 wt % determined by the method as described in Example 1.

Preparation 3 The Production of PEG530-PCL2000-PEG530 Tri-Block Copolymer

Suitable amount of DBTDL was added to 100 g (0.182 mole) of methoxy-polyethylene glycol (molecular weight=550) dissolved in 200 ml of DMF, immediately followed by the addition of 29 g (0.173 mole) of HDI. The temperature was set at 50° C. and the reaction was performed in a nitrogen atmosphere. After 5 hours of reaction, 172.9 g (0.0865 mole) of PCL-diol (molecular weight=2000) was added, the temperature was raised to 100° C., and the reaction was continued overnight. Then, the reaction was quenched by DBA. After the resultant was cooled down, it was precipitated by 1000 ml of ether, and the resulting precipitates were dissolved in DMF and precipitated from ether. Such precipitation process was repeated three times. Then the precipitates were vacuumed until dry, yielding a PEG530-PCL2000-PEG530 tri-block copolymer.

The CMC of the product was about 0.013 wt % determined by the method as described in Example 1.

Figure 3:
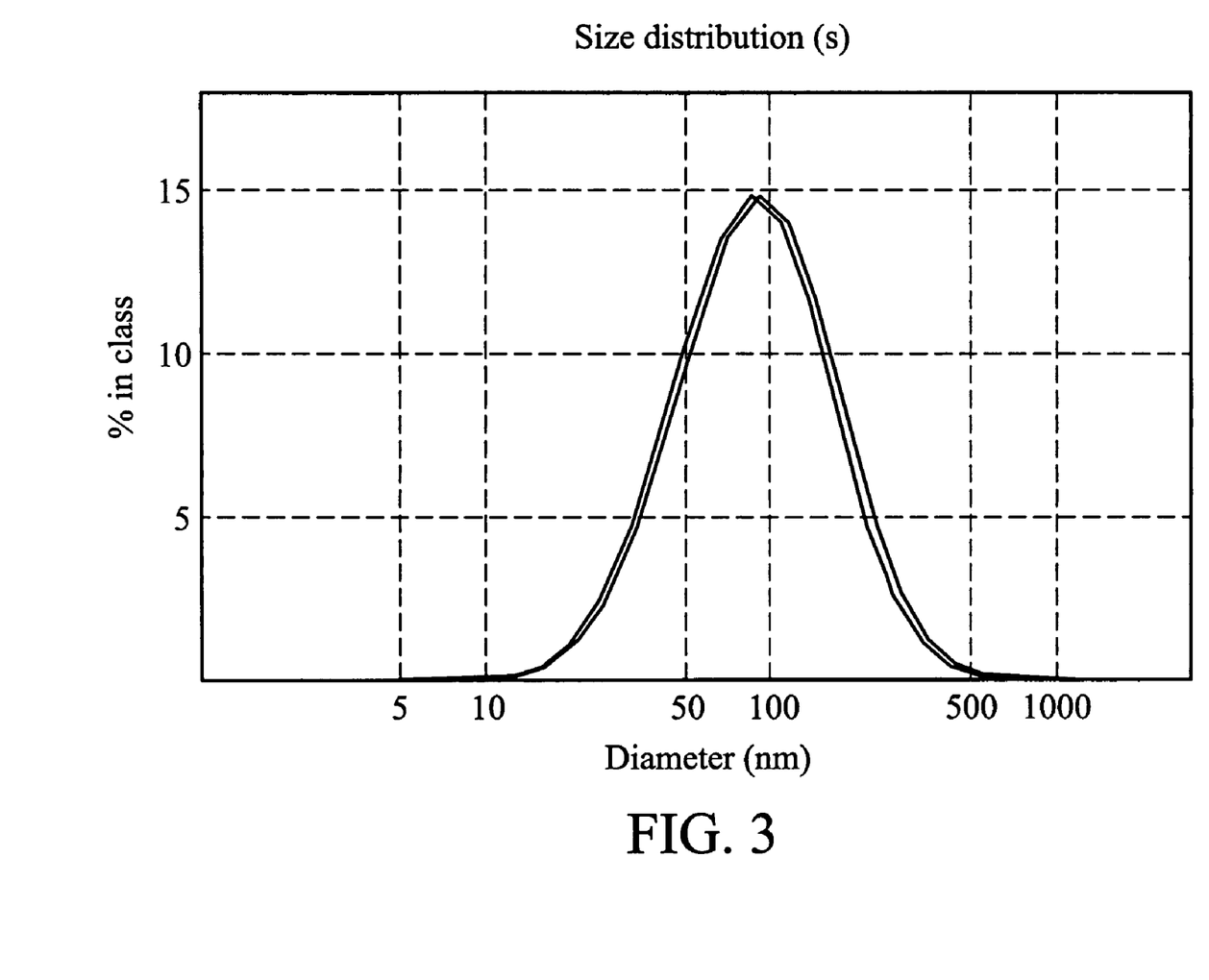
FIG. 3 is a plot showing the result of the determination of the diameter of the micelles formed from PEG530-PCL2000-PEG530 tri-block copolymer in the aqueous medium obtained from Preparation 3.

The size of the resulting micelles was determined using a dynamic light scattering instrument (Malvern UK+44 of Malvern Instruments Company) to be about 85 nm, as shown in FIG. 3.

Preparation 4 The Production of PEG2000-PCL2000-PEG2000 Tri-Block Copolymer

Suitable amount of DBTDL was added to 100 g (0.05 mole) of methoxy-polyethylene glycol (molecular weight=2000) dissolved in 200 ml of DMF, immediately followed by the addition of 7.98 g (0.0475 mole) of HDI. The temperature was set at 50° C. and the reaction was performed in a nitrogen atmosphere. After 5 hours of reaction, 47.5 g (0.02375 mole) of PCL-diol (molecular weight=2000) was added, the temperature was raised to 100° C., and the reaction was continued overnight. Then, the reaction was quenched by DBA. After the resultant was cooled down, it was precipitated by 1000 ml of ether, and the resulting precipitates were dissolved in DMF and precipitated from ether. Such precipitation process was repeated three times. Then the precipitates were vacuumed until dry, yielding a PEG2000-PCL2000-PEG2000 tri-block copolymer.

The CMC of the product was about 0.043 wt % determined by the method as described in Example 1.

Preparation 5 The Production of PEG4600-PCL2000-PEG4600 Tri-Block Copolymer

Suitable amount of DBTDL was added to 100 g (0.022 mole) of methoxy-polyethylene glycol (molecular weight=4600) dissolved in 200 ml of DMF, immediately followed by the addition of 3.53 g (0.021 mole) of HDI. The temperature was set at 50° C. and the reaction was performed in a nitrogen atmosphere. After 5 hours of reaction, 22 g (0.011 mole) of PCL-diol (molecular weight=2000) was added, the temperature was raised to 100° C., and the reaction was continued overnight. Then, the reaction was quenched by DBA. After the resultant was cooled down, it was precipitated by 1000 ml of ether, and the resulting precipitates were dissolved in DMF and precipitated from ether. Such precipitation process was repeated three times. Then the precipitates were vacuumed until dry, yielding a PEG4600-PCL2000-PEG4600 tri-block copolymer.

The CMC of the product was about 0.0789 wt % determined by the method as described in Example 1.

The size of the resulting micelles was determined using a dynamic light scattering instrument to be about 85 nm.

According to the result from the determination of the critical micelle concentration as mentioned above, it is shown that all of the products obtained from Examples 1 to 6 and Preparations 1 to 5 can form micelles and these micelles are the biodegradable polymeric micelle compositions of the present invention, which were demonstrated to have an ability to encapsulate hydrophobic compounds and can be further employed to encapsulate hydrophobic drugs and bioactive substances.

Examples 7 to 9

The Application of the Copolymer to Drug Encapsulation

Example 7

PEG2000-PCL530-PEG2000 Tri-Block Copolymer Encapsulating Paclitaxel 30 mg of paclitaxel and 150 mg of PEG2000-PCL530-PEG2000 tri-block copolymer were dissolved in 2 ml of acetonitrile. The resulting mixture was vacuumed at 60° C. by means of rotary evaporation to form a colloid. Pure water was added to the colloid at 60° C., forming micelles encapsulating the drug. The resultant was filtered through 0.22 μm filter to remove the impurities in the water and freeze-dried, forming a drug delivery composition.

Example 8

PEG2000-PCL2000-PEG2000 Tri-Block Copolymer Encapsulating Paclitaxel

Example 8 was performed using the method same as Example 7, provided that 150 mg of PEG2000-PCL2000-PEG2000 tri-block copolymer was used instead of PEG2000-PCL530-PEG2000 tri-block copolymer, forming a drug delivery composition.

Example 7

PEG2000-PCL530-PEG2000 Tri-Block Copolymer Encapsulating Paclitaxel

Example 9 was performed using the method same as Example 7, provided that 150 mg of PEG530-PCL2000-PEG530 tri-block copolymer was used instead of PEG2000-PCL530-PEG2000 tri-block copolymer, forming a drug delivery composition.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biodegradable polymeric micelle composition, comprising:
   (a) a copolymer having the formula:

C—(S)$_n$ wherein C is a core block comprising a bioresorbable hydrophobic polyester segment coupled to a polyol initiator, S is a shell block comprising a hydrophilic polyethylene glycol segment, n is 3, the hydrophobic polyester segment and the hydrophilic polyethylene glycol segment are linked by hexamethylene diisocyanate, and the copolymer is a star copolymer; and
   (b) an aqueous medium;
   wherein the copolymer is dispersed in the aqueous medium to form micelles, the bioresorbable hydrophobic polyester segment has an average molecular weight of between 200 and 10,000, and the copolymer dispersed in the aqueous medium has a concentration of 0.001 weight percent, 0.005 weight percent, 0.01 weight percent, 0.025 weight percent, 0.05 weight percent or 0.1 weight percent.

2. The composition as claimed in claim 1, wherein the bioresorbable hydrophobic polyester segment has an average molecular weight of between 250 and 5000.

3. The composition as claimed in claim 1, wherein the hydrophilic polyethylene glycol segment has an average molecular weight of between 200 and 10000.

4. The composition as claimed in claim 1, wherein the hydrophilic polyethylene glycol segment has an average molecular weight of between 250 and 7000.

5. The composition as claimed in claim 1, wherein the bioresorbable hydrophobic polyester is a homopolymer or copolymer synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, γ-butyrolactone, γ-hydroxy butyric acid, δ-valerolactone, δ-hydroxy valeric acid, hydroxybutyric acids, and malic acid.

6. The composition as claimed in claim 1, wherein the bioresorbable hydrophobic polyester is polycaprolactone.

7. The composition as claimed in claim 1, wherein the micelle has a size between 1 nm and 800 nm.

8. The composition as claimed in claim 1, which can be used for the encapsulation of a hydrophobic compound.

9. The composition as claimed in claim 8, wherein the hydrophobic compound is a pharmaceutical compound.

10. The composition as claimed in claim 9, wherein the pharmaceutical compound is selected from the group consisting of protein complexes, gene drugs, hormone drugs, and anti-cancer drugs.

11. The composition as claimed in claim 1, wherein the bioresorbable hydrophobic polyester is a homopolymer or copolymer synthesized from monomers selected from the group consisting of ε-hydroxy hexonoic acid, γ-butyrolactone, γ-hydroxy butyric acid, δ-valerolactone, δ-hydroxy valeric acid, hydroxybutyric acids, and malic acid.

12. A method for forming a biodegradable copolymer, comprising:
   forming a core block by coupling a bioresorbable hydrophobic polyester and a polyol initiator;
   forming a shell block by coupling a hydrophilic polyethylene glycol and an urethane linkage; and
   forming a star polymer by linking the core block and the shell block;
   wherein the star polymer has a formula:

C—(S)$_n$ wherein C is the core block, S is the shell block, n is 3, the bioresorbable hydrophobic polyester segment has an average molecular weight of between 200 and 10,000, the bioresorbable hydrophobic polyester and the hydrophilic polyethylene glycol are linked by hexamethylene diisocyanate, and the copolymer dispersed in the aqueous medium has a concentration of 0.001 weight percent, 0.005 weight percent, 0.01 weight percent, 0.025 weight percent, 0.05 weight percent or 0.1 weight percent.

13. The method as claimed in claim 12, wherein the bioresorbable hydrophobic polyester segment has an average molecular weight of between 250 and 5000.

14. The method as claimed in claim 12, wherein the hydrophilic polyethylene glycol segment has an average molecular weight of between 200 and 10000.

15. The method as claimed in claim 12, wherein the hydrophilic polyethylene glycol segment has an average molecular weight of between 250 and 7000.

16. The method as claimed in claim 12, wherein the bioresorbable hydrophobic polyester is a homopolymer or copolymer synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, γ-butyrolactone, γ-hydroxy butyric acid, δ-valerolactone, δ-hydroxy valeric acid, hydroxybutyric acids, and malic acid.

17. The method as claimed in claim 16, wherein the bioresorbable hydrophobic polyester is polycaprolactone.

18. The composition as claimed in claim 1, wherein the copolymer dispersed in the aqueous media has a concentration of 0.05 weight percent.

19. The composition as claimed in claim 1, wherein the copolymer dispersed in the aqueous media has a concentration of 0.01 weight percent.

20. The method as claimed in claim 12, wherein the copolymer dispersed in the aqueous media has a concentration of 0.05 weight percent.

21. The method as claimed in claim 12, wherein the copolymer dispersed in the aqueous media has a concentration of 0.01 weight percent.

* * * * *

UNITED STATES PATENT AND TRADEMARK OFFICE
CERTIFICATE OF CORRECTION

PATENT NO. : 7,655,258 B2
APPLICATION NO. : 10/745975
DATED : February 2, 2010
INVENTOR(S) : Tsai et al.

It is certified that error appears in the above-identified patent and that said Letters Patent is hereby corrected as shown below:

Title page item [56] change "(CN)" to --(TW)--.

Column 1, line 7, change "Republic of China" to --Taiwan--.

Signed and Sealed this
Fifteenth Day of May, 2012

David J. Kappos
*Director of the United States Patent and Trademark Office*